(12) United States Patent
Hestad et al.

(10) Patent No.: US 7,419,506 B2
(45) Date of Patent: Sep. 2, 2008

(54) ARTIFICIAL SPINAL DISCS AND METHODS

(75) Inventors: Hugh D. Hestad, Edina, MN (US); John F. Otte, St. Anthony, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 189 days.

(21) Appl. No.: 11/283,189

(22) Filed: Nov. 18, 2005

(65) Prior Publication Data

US 2007/0118225 A1 May 24, 2007

(51) Int. Cl.
*A61F 2/44* (2006.01)
*A61B 17/56* (2006.01)

(52) U.S. Cl. .................. 623/17.16; 623/17.14

(58) Field of Classification Search .... 623/17.11–17.16
See application file for complete search history.

(56) References Cited

U.S. PATENT DOCUMENTS

| | | | |
|---|---|---|---|
| 5,171,281 A | | 12/1992 | Parsons et al. |
| 5,236,460 A | * | 8/1993 | Barber ..................... 623/17.15 |
| 5,370,697 A | * | 12/1994 | Baumgartner ............ 623/17.15 |
| 5,375,823 A | * | 12/1994 | Navas ...................... 623/17.15 |
| 5,674,294 A | | 10/1997 | Bainville et al. |
| 5,989,291 A | | 11/1999 | Ralph et al. |
| 6,033,438 A | | 3/2000 | Bianchi et al. |
| 6,093,205 A | | 7/2000 | McLeod et al. |
| 6,136,031 A | | 10/2000 | Middleton |
| 6,139,579 A | | 10/2000 | Steffee et al. |
| 6,443,437 B1 | * | 9/2002 | Beyene et al. ............ 267/64.26 |
| 6,533,818 B1 | | 3/2003 | Weber et al. |
| 6,582,468 B1 | | 6/2003 | Gauchet |
| 6,723,127 B2 | | 4/2004 | Ralph et al. |
| 6,770,095 B2 | * | 8/2004 | Grinberg et al. ......... 623/17.14 |
| 7,029,475 B2 | * | 4/2006 | Panjabi ........................ 606/61 |
| 7,066,957 B2 | * | 6/2006 | Graf ........................ 623/17.12 |
| 2002/0035400 A1 | | 3/2002 | Bryan et al. |
| 2004/0098130 A1 | | 5/2004 | Ralph et al. |

* cited by examiner

*Primary Examiner*—Pedro Philogene
(74) *Attorney, Agent, or Firm*—Crompton, Seager & Tufte LLC.

(57) ABSTRACT

An artificial disc includes a top vertebra-attachment portion and a lower spacer support connected to the top vertebra-attachment portion; a bottom vertebra-attachment portion and an upper spacer support connected to the bottom vertebra-attachment portion. The spacer supports are disposed between the vertebra-attachment portions, and the lower spacer support is disposed between the bottom vertebra-attachment portion and the upper spacer support. The disc further includes a first elastic spacer positioned between the spacer supports for compressively resisting tensile loading of the disc; and a second spacer disposed between the bottom vertebra-attachment portion and the lower spacer support or between the top vertebra-attachment portion and the upper spacer support for compressively resisting compressive loading of the disc.

20 Claims, 4 Drawing Sheets

ARTIFICIAL SPINAL DISCS AND METHODS

TECHNICAL FIELD

The present invention relates to spinal disc implants. More particularly, the present invention relates to an artificial spinal disc.

BACKGROUND

Artificial spinal discs have been used to replace native spinal discs that are diseased, injured or otherwise weakened. Examples of traditional artificial discs include articulating discs, wherein a disc implant typically has two halves that are pivotally connected to each other, and elastic discs, wherein an implant typically comprises one or more pieces of elastic materials, in some cases attached to endplates that are affixed to their respective vertebrae.

The elastic discs have an advantage over articulating discs in that the former in many cases provide more shock absorption and more closely approximate the motion states of a natural disc because modes of displacement are not limited to tilting. However, traditional elastic discs may experience certain failure modes that adversely affect the performance of the discs. For example, in elastic discs where the elastic material is attached to endplates that are affixed to the vertebrae, the elastic material may completely or partially detach from the endplates as a result of repeated tensile stress, thereby losing all or some of the tensile strength of the disc. Elastic materials themselves may deteriorate, by, for example, developing stress cracks, under tensile loading. In addition, certain elastic materials have more desirable properties under compressive loading than under tensile loading.

There is thus a need for an improved artificial disc utilizing elastic materials that reduces deterioration from tensile loading.

SUMMARY

The invention disclosed herein is aimed at providing an improved artificial spinal disc and method of making and using the same. In one aspect of the invention, an artificial spinal disc includes an upper member having a top vertebra-attachment portion and a lower spacer support connected to the top vertebra-attachment portion; a lower member having a bottom vertebra-attachment portion an upper spacer support connected to the bottom vertebra-attachment portion. The spacer supports are disposed between the vertebra-attachment portions, and the lower spacer support is disposed between the bottom vertebra-attachment portion and the upper spacer support. The artificial spinal disc further includes an elastic spacer positioned between the spacer supports. The spacer supports thus compress the first elastic spacer when the disc is tensilely loaded, i.e., when the vertebra-attachment portions are biased away from each other.

An additional elastic spacer can be positioned in either the space between the top vertebra-attachment portion and the upper spacer support or the space between the bottom vertebra-attachment portion and the lower spacer support. The additional spacer is therefore compressed when the disc is compressively loaded.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

BRIEF DESCRIPTION OF THE DRAWINGS

These and other features, aspects, and advantages of the present invention will become better understood with regard to the following description, appended claims, and accompanying drawings where:

DETAILED DESCRIPTION OF ILLUSTRATIVE EMBODIMENTS

Figure 1:
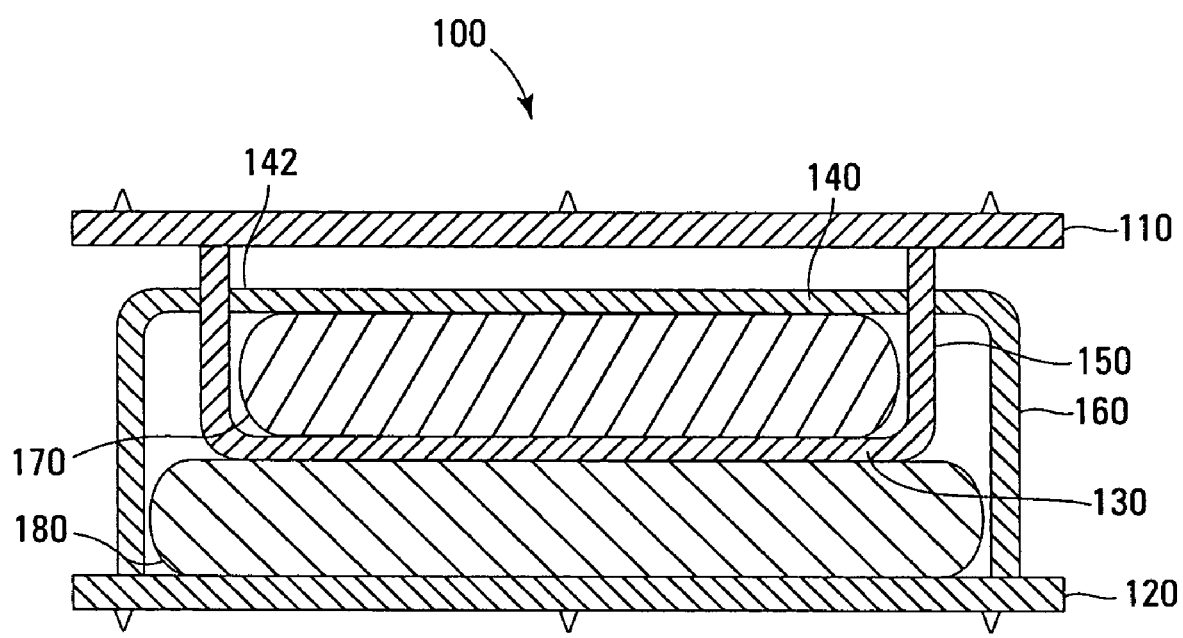
FIG. 1 is a cross-sectional view of a first embodiment of the invention.

A first embodiment of the invention, illustrated in FIG. 1, is an artificial spinal disc 100 for implantation between two neighboring vertebrae (not shown) above and below the disc 100. The disc 100 may be adapted for use in both the lumbar and cervical regions of the spine.

The disc 100 has a top endplate 110 as a vertebra-attachment portion for securing the disc 100 to the vertebra above, and a bottom endplate 120 as a vertebra-attachment portion for securing the disc 100 to the vertebra below. The disc 100 also includes a lower medial plate 130, which is connected to the top endplate 110, and an upper medial plate 140 connected to the bottom endplate 120. The lower medial plate 130 is attached to the top endplate 110 by connecting rods 150, which extend through holes 142 in the upper medial plate 140. The upper medial plate 140 is attached to the bottom endplate 120 by connecting rods 160, which extend outside the lower medial plate 130. Other configurations can also be used. For example, the connecting rods 150 can also be positioned to extend outside the upper medial plate 140, with the connecting rods 150 and 160 horizontally offset from each other. Furthermore, the upper and lower medial plates 140 and 130 may be integrally formed with the bottom and top endplates 120 and 110, respectively.

The spinal disc 100 thus has two frame members that are interlocked but can move relative to each other. The upper member includes the top endplate 110 and the lower medial plate 130; the lower member includes the bottom endplate 120 and the upper medial plate 140. When the endplates 110, 120 move apart, the medial plates 130, 140 move closer to each other; when the endplates 110, 120 move closer to each other, the distance between the top endplate 110 and the upper medial plate 140 decreases, and so does the distance between the bottom endplate 120 and the lower medial plate 130.

In this illustrative embodiment, a first elastic spacer 170 is positioned between the two medial plates, which act as spacer supports. A second elastic spacer 180 is positioned between the lower medial plate 130 and the bottom endplate 120. Each spacer is attached to at most one of the plates or can be not attached to any plate and be confined inside the artificial disc 100 by the connecting rods 150 and/or 160. Because of the above-described relationship between the inter-plate distances and the relative movement between the endplates, the first spacer 170 is under compression when the endplates 110, 120 are pulled apart, i.e., when the disc 100 is under tensile loading. Such tensile loading may be exerted in various regions of the disc 100 as the wearer flexes and extends the spine. In addition, the second spacer 180 is under compression when the disc 100 is under compressive loading. Such compressive loading may be exerted by gravity as the disc 100 is a load bearing member, and also as the wearer flexes and extends the spine. Thus, the disc 100 may undergo both tensile loading and compressive loading at the same time. Because each of the spacers 170, 180 is attached to at most only one plate, the spacers 170, 180 do not experience any tensile loading whether the disc 100 is under compressive or tensile loading. The risk of failure of the spacers themselves or their attachment to any plates due to tensile stress is therefore greatly reduced or eliminated.

The spacers 170, 180 are solid blocks in form and made of an elastomer in this illustrative embodiment but can be of any other shape and made of any other material to achieve the desired design. For example, the spacers 170, 180 can be made of a thermoplastic elastomer, such as polycarbonate urethane (PCU), a thermoset elastomer, such as silicon, a hydrogel or a metal, which can be configured as a coil spring, a leaf spring or other suitable forms to achieve the desired compliance.

In operation, the spacers 170, 180 can be sized to be under a certain desired amount of compression before implantation. The desired amount can be ascertained from the desired states of compression of both spacers 170, 180 in a given position (e.g., lying down or standing) of the patient, with the disc 100 implanted. A space for disc implantation is created by removing at least part of the natural disc to be replaced. The disc 100, which can be pre-compressed to be shorter than the height of the implantation space, is then inserted into the space.

Figure 2:
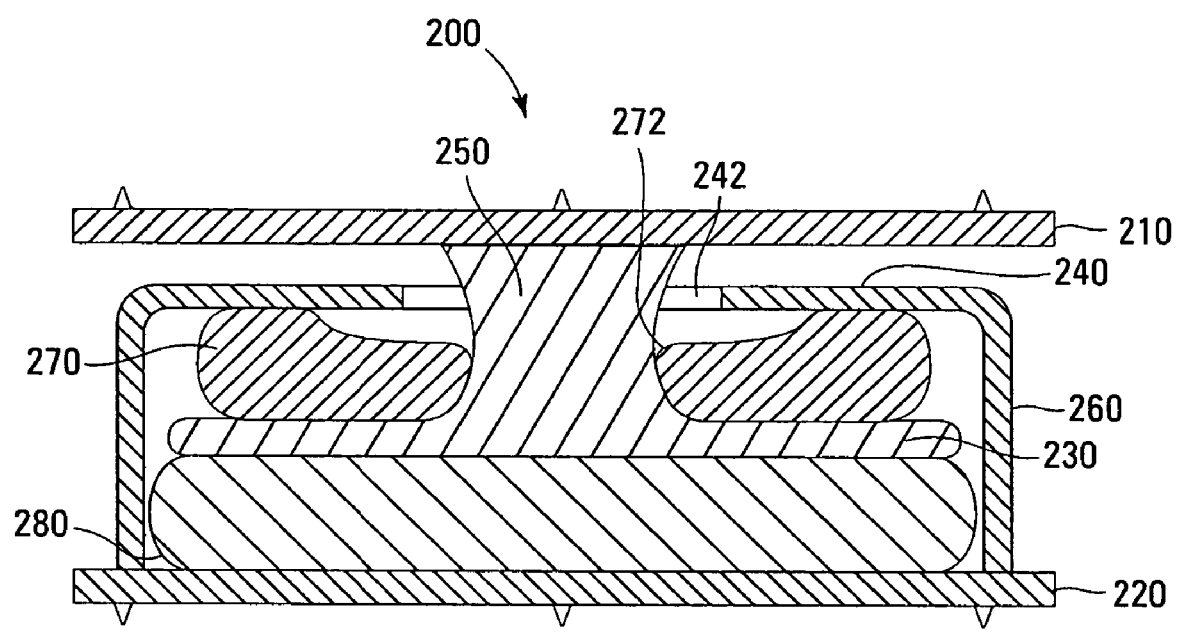
FIG. 2 is a cross-sectional view of a second embodiment of the invention.

Referring to FIG. 2, in a second embodiment of the invention, an artificial spinal disc 200 is similar to the disc 100 shown in FIG. 1 in that the disc 200 also includes the top endplate 210, bottom endplate 220, lower medial plate 230, upper medial plate 240; first spacer 270 and second spacer 280. The spatial relationship among these components is also similar to that in disc 100. However, whereas the upper medial plate 240 is connected to the bottom endplate 220 by connecting rods 260 as in the first embodiment of the invention, the lower medial plate 230 is connected to the top endplate 210 by a center post 250, which passes through a hole 242 in the upper medial plate 240 and a hole 272 in the first spacer 270. The ring-shaped first spacer 270 is thus secured in between the two medial plates 230, 240 without the need to be attached to either plate.

Figure 3:
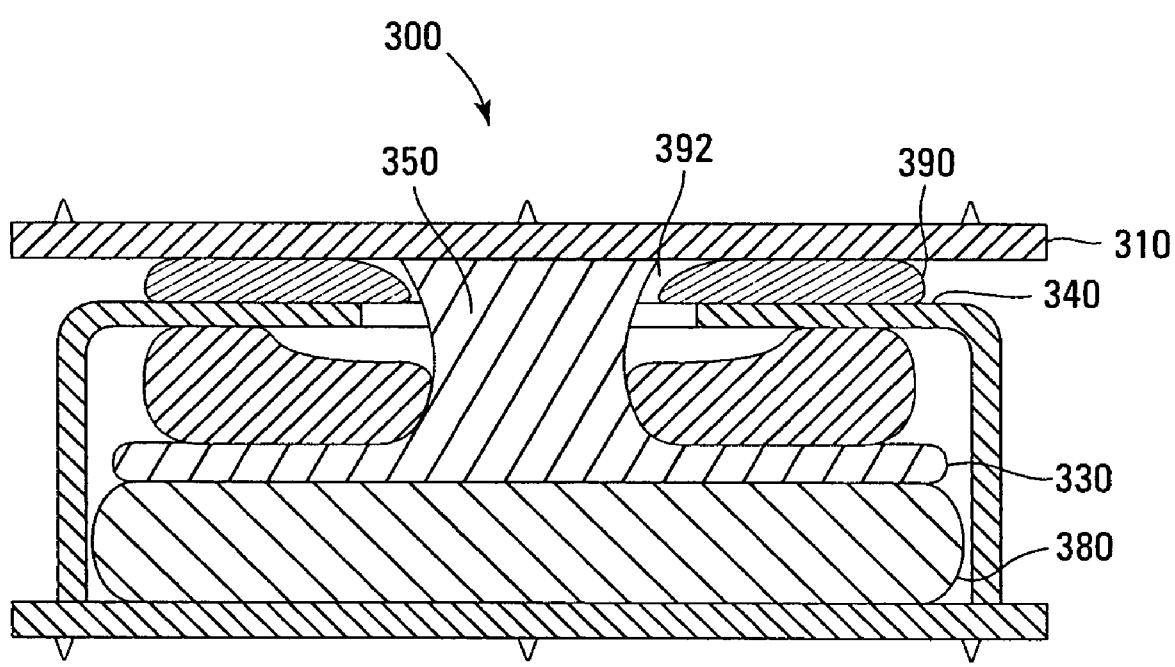
FIG. 3 is a cross-sectional view of a third embodiment of the invention.

Referring to FIG. 3, in a third embodiment of the invention, an artificial spinal disc 300 is similar to the disc 200 described above but with a third elastic spacer 390 disposed between the top endplate 310 and the upper medial plate 340. The third spacer 390 had a hole 392 to accommodate the post 350, which connects the lower medial plate 330 to the top endplate 310, and is thus secured in place by the post 350. Both the second spacer 380 and the third spacer 390 are compressed when the disc 300 is under compressive loading.

Additional configurations can be used to achieve an artificial disc with spacers that only experience compressive stress. For example, a spacer (not shown) extending between the two endplates can be used for resisting compressive loading of the disc. The spacer can be, for example, an annular spacer surrounding another spacer positioned between the two medial plates.

Figure 4:
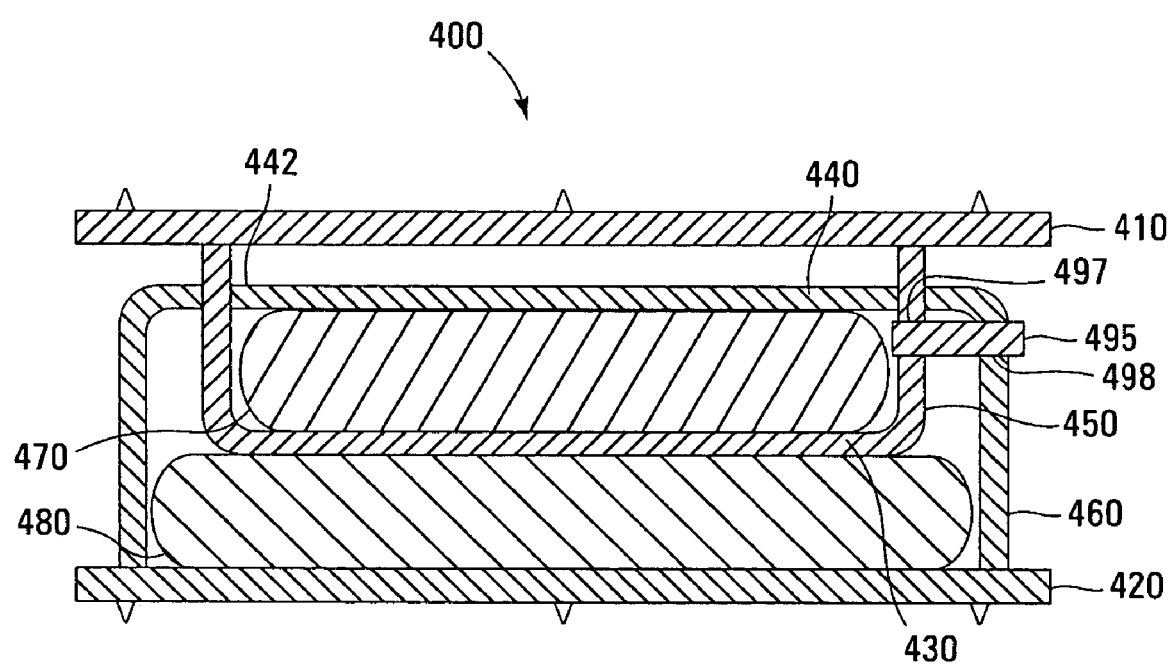
FIG. 4 is a cross-sectional view of a fourth embodiment of the invention.

In one embodiment, the artificial disc is provided with means for pre-compressing the artificial disc to be shorter than the height of the implantation space. FIG. 4 shows one possible embodiment, in which an artificial disc 400, generally similar to artificial disc 100 of FIG. 1, is provided with a retainer pin 495 for engaging apertures 497 and 498 in connecting rods 450 and 460. Apertures 497 and 498 are positioned such that when aligned with one another to receive pin 495, second spacer 480 is compressed between the bottom endplate 420 and lower medial plate 430. After the artificial disc 400 is positioned between first and second vertebral bodies, pin 495 is removed. Other means for pre-compressing or compressively loading the artificial disc 400 may be used, including, for example, clamps and turnkey assemblies.

In still other embodiments, the artificial disc may be positioned between the first and second vertebral bodies without one or all of the spacers, thus reducing the vertical height or profile of the artificial disc. After installation, the spacers are inserted into the artificial disc.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. An artificial spinal disc for implantation within a disc space between first and second opposing vertebrae, comprising:
   a first member having a first vertebra-attachment plate for attaching to the first vertebra within the disc space and a first spacer support connected to the first vertebra-attachment plate;
   a second member having a second vertebra-attachment plate for attaching to the second opposing vertebra within the disc space and a second spacer support connected to the second vertebra-attachment plate, the spacer supports being disposed between the vertebra-attachment plates, and the first spacer support being disposed between the second vertebra-attachment plate and the second spacer support; and
   a first elastic spacer positioned between the spacer supports,
   whereby the spacer supports compress the first elastic spacer when the vertebra-attachment plates are biased away from each other.

2. The artificial spinal disc of claim 1, further comprising a second elastic spacer, positioned between the first vertebra-attachment plate and the second spacer support.

3. The artificial disc of claim 2, further comprising a third elastic spacer, positioned between the second vertebra-attachment plate and the first spacer support.

4. The artificial disc of claim 1, further comprising an elastic spacer extending from the first vertebra-attachment plate to the second vertebra-attachment plate.

5. The artificial disc of claim 1, wherein the first elastic spacer comprises a thermoplastic elastomer or a hydrogel.

6. The artificial disc of claim 1, wherein the first elastic spacer comprises a metal spring.

7. The artificial disc of claim 1, wherein the first spacer support is connected to the first vertebra-attachment plate by a post, and the first elastic spacer surrounds the post.

8. The artificial disc of claim 1, further comprising means for pre-compressing the artificial disc.

9. The artificial disc of claim 1, wherein the first member and the second member are interlocked with one another.

10. An artificial spinal disc for implantation within a disc space between first and second opposing vertebrae, comprising:
   a first member having a first vertebra-attachment plate for attaching to the first vertebra within the disc space and a first spacer support connected to the first vertebra-attachment plate;
   a second member having a second vertebra-attachment plate for attaching to the second opposing vertebra within the disc space and a second spacer support connected to the second vertebra-attachment plate, the spacer supports being disposed between the vertebra-attachment plates, and the first spacer support being disposed between the second vertebra-attachment plate and the second spacer support; and
   a first elastic spacer positioned between the first vertebra-attachment plate and the second spacer support,
   whereby the spacer supports compress the first elastic spacer when the vertebra-attachment plate are biased away-from toward each other.

11. The artificial spinal disc of claim 10, further comprising a second elastic spacer, positioned between the spacer supports.

12. The artificial spinal disc of claim 11, further comprising a third elastic spacer, positioned between the second vertebra-attachment plate and the first spacer support.

13. The artificial spinal disc of claim 10, further comprising an elastic spacer extending from the first vertebra-attachment plate to the second vertebra-attachment plate.

14. The artificial spinal disc of claim 10, wherein the first elastic spacer comprises a thermoplastic elastomer or a hydrogel.

15. The artificial spinal disc of claim 10, wherein the first elastic spacer comprises a metal spring.

16. The artificial disc of claim 10, wherein the first spacer support is connected to the first vertebra-attachment plate by a post, and the first elastic spacer surrounds the post.

17. A method of implanting an artificial spinal disc, the method comprising the steps of:
   removing at least a portion of a natural spinal disc from between first and second adjacent vertebral bodies;
   positioning an artificial spinal disc between the first and second vertebral bodies within the disc space, the artificial spinal disc comprising:
      a first member having a first vertebra-attachment plate and a first spacer support connected to the first vertebra-attachment plate;
      a second member having a second vertebra-attachment plate and a second spacer support connected to the second vertebra-attachment plate, the spacer supports being disposed between the vertebra-attachment plates, and the first spacer support being disposed between the second vertebra-attachment plate and the second spacer support; and
      a first elastic spacer positioned between the spacer supports;
   securing the first vertebra-attachment portion to the first vertebra; and
   securing the second vertebra-attachment portion to the second vertebra.

18. The method of claim 17, wherein the artificial disc further comprises a second elastic spacer, positioned between the first vertebra-attachment plate and the second spacer support.

19. The method of claim 18, further comprising compressing the first elastic spacer by tensilely loading the artificial spinal disc; and compressing the second elastic spacer by compressively loading the artificial spinal disc.

20. The method of claim 18, further comprising pre-compressing the second elastic spacer by compressively loading the artificial spinal disc prior to positioning the artificial disc between the first and second vertebral bodies.

* * * * *